United States Patent [19]

Bianco

[11] Patent Number: 4,908,382
[45] Date of Patent: Mar. 13, 1990

[54] METHOD FOR TREATING ASTHMA

[75] Inventor: Sebastiano Bianco, Milan, Italy

[73] Assignee: Hoechst Aktiengesellschaft, Frankfurt am Main, Fed. Rep. of Germany

[21] Appl. No.: 308,070

[22] Filed: Feb. 9, 1989

[51] Int. Cl.$^4$ .......................... A61K 9/14; A61K 9/72; A61K 31/34
[52] U.S. Cl. .................................................. 514/471
[58] Field of Search ........................................ 514/471

[56] References Cited

U.S. PATENT DOCUMENTS 4,663,322  5/1987  Beyer ................................... 514/222
4,686,217  8/1987  Baxter et al. ........................ 514/210

Primary Examiner—Shep K. Rose
Attorney, Agent, or Firm—Finnegan, Henderson, Farabow, Garrett and Dunner

[57] ABSTRACT

Inhaled furosemide is an effective agent for preventing asthma attacks.

3 Claims, 1 Drawing Sheet

METHOD FOR TREATING ASTHMA

A diverse array of therapeutic agents are used today both in the prophylaxis und treatment of asthma. Asthma can be induced by a wide range of stimuli whose pathogenetic mechanisms are complex and not yet fully understood.

Furosemide is a well known diuretic agent of the formula I

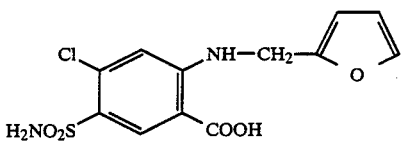

and its effects have been studied extensively. The drug is usually given orally but can be used intravenously to promote diuresis.

On the other hand various methods for preventing or treating asthma are known all of them being more or less effective. Despite of the existence of medicaments for the treatment of asthma it is desirable to improve the antiasthmatics be it by preventing an asthma attack be it by combating it.

This was accomplished by a method of treating asthma which consists in inhaling furosemide. This method proved to be highly effective. It is very surprising that inhaled furosemide acts to suppress asthma whereas furosemide administered in the usual manner for instance orally showed no effect at all.

In this novel use of furosemide, the drug is administered in a nebulized solution containing ®Lasix (Hoechst) 10 mg/ml with NaCl 7 mg, NaOH to pH 9 and water to make up 1 ml. Based on an adult weighing 75 kg, single doses range from approximately 0.1 mg to 50 mg, preferably from 1 mg to 20 mg furosemide which can be administered on multiple occasions over 24 hours.

According to the invention the furosemide is administered to the patient by inhalation in a solution in water which contains additional appropriate substances, such as NaCl and the pH of which is about 9 as usual in solutions of furosemide.

The applied single doses range from 0.1, preferably 1 mg, up to 50 mg, preferably 20 mg furosemide, related to an adult of a weight of about 75 kg.

These doses can be administered once, twice or more times per 24 hours.

The following studies show the antiasthmatic effect of furosemide in preventing bronchoconstriction.

1. Inhaled Furosemide (F) is highly effective in the prevention of exercise-induced bronchoconstriction:

SUBJECTS AND METHODS

Single-dose Study 18 clinically stable non-smokers (15 men, 3 women) aged 10–40 years (mean 20), with a typical history of exercise-induced wheezing and no other diseases gave informed consent for the study. All had been free of symptoms of respiratory infections for at least 6 weeks and were well controlled with inhaled $\beta_2$-stimulants; only 7 also needed inhaled corticosteroids. Both drugs were withheld for at least 8 h before each exercise challenge. The subjects had undergone two screening tests 2 days apart to qualify for entry to the study. On the first occasion, after resting for 20 min and after wearing a nose clip, patents were invited to run at regular, sub-maximum speed back and forth along a 60 m straight corridor near the laboratory for 5–9 min; they could stop at any time during this interval if tired. Number of corridor lengths run and duration of exercise were recorded. $FEV_1$ (forced expiratory volume at 1 second) was measured at rest and 5 and 10 min after exercise. Arterial pressure and pulse rate were taken immediately before and immediately after excerise. The second screening test was to confirm that $FEV_1$ fall was at least 20%; on this occasion $FEV_1$ was measured at the same time intervals as in the study days and this was taken as the control test.

The study was performed on 2 consecutive days 3–5 days after the second screening test.

At the same time on each of the 2 days subjects were asked to inhale furosemide or placebo before exercise. These agents were given in random order and double blind. Furosemide (®Lasix Hoechst, as a 10 mg/ml solution containing NaCl 7.0 mg, NaOH to reach pH 9, and water to make up 1 ml) and placebo (the diluent solution) were given by means of a jet nebuliser driven by a small compressor ('Flatus', MEFAR, 20073 Bovezzo, Brescia, Italy). Patients inhaled from the nebuliser for 20 min, during which time the mean amount of furosemide delivered to the mouth (calculated on five occasions by differential weighing after placing 4 ml furosemide solution in the reservoir) was 28.3 (SEM 0.6) mg. For ease of data presentation this dose was designated F 28. Patients were connected to the nebuliser through a plastic cylindrical mouth-piece and asked to breathe normally wearing a nose-clip. $FEV_1$ was measured with a water-sealed spirometer (Warren E. Collins) in duplicate and the better value recorded. Measurements were made immediately before and after aerosol inhalation and then 2, 4, 6, 8, 15 and 30 mins after exercise.

Two-dose Study 8 clinically stable non-smokers (7 men, 1 women), aged 13–38 years (mean 17), with a typical history of exercise-induced wheezing participated in this study. All were taking inhaled $\beta_2$-stimulants and 4 also needed inhaled corticosteroids. The admission criteria were the same as for the single-dose study. The protocol differed from the previous one only in that two doses of furosemide—14 mg (F14) and 28 mg were tested. Thus there were 3 study days instead of two. Both volume of liquid in the reservoir (4 ml) and nebulisation time (20 min) were kept constant; the furosemide preparation for the F14 dose contained half the amount of drug for the F28 dose.

Oral Furosemide Study

The amount of furosemide delivered to the mouth in the single-dose study was 28 mg. Since approximately 20% of this dose would have been exhaled and no more than 10% would have been deposited in the bronchial tree, (Lewis RA. Therapeutical aerosols. In: Cummings G, Bonsignore G, eds. Drugs and lung. E Maiorana International Science Series, Life Sciences vol 14, New York: Plenum, 1983, 63–83 and Newhouse MT, Dolovich MB. Control and asthma by aerosols. N Engl J Med 1986; 315: 870–74) approximately 20 mg would have been ingested. To ascertain whether 20 mg furosemide given orally could, at least in part, account for the observed protective effect, 8 clinically stable non-smokers (all men), 16 to 30 years of age (mean 21), who fulfilled the same selection criteria as for the single and two-dose studies, were investigated. Before exercise, subjects were given, in random order and double blind, (a) inhaled furosemide (F28)+oral placebo (three sips, each of 3 ml, of the diluent solution, one at the beginning, one in the middle, and one at the end of the nebulisation period); (b) inhaled placebo+oral furosemide (20 mg in 9 ml—three 3 ml sips—of the diluent solution); (c) inhaled placebo+oral placebo. All mesurements (arterial pressure, pulse rate, and $FEV_1$) were made at the same time intervals as in the previous tests.

In all phases of the study a variability of baseline $FEV_1$ was kept at less than 10% during the study days by admitting only stable patients and by excluding those who after the preliminary tests showed a variability of more than 10%. 11 patients in the first group, 4 in the second and 2 in the third were atopic, with positive skin tests to Dermatophagoides pteronyssinus and/or grass mixture. Those allergic to the grass mixture (patients 10, 4 and 2, respectively) were examined out of the pollen season.

Analysis of Data

Baseline (before and after treatment) values (mean 95% CI) of $FEV_1$ were expressed in absolute terms as a percentage of predicted (Bates DV, Macklem PT, Christie RV. Respiratory function in disease, 2nd ed. Philadelphia: Saunders, 1971: 93-94); postexercise values were expressed as absolute and percentage changes from post-treatment baseline at individual time points. Also the maximum percentage falls in $FEV_1$ from post-treatment baseline values were calculated.

The paired Student's t test was used for comparison. A value of $p<0.05$ was considered significant.

RESULTS

Single-dose Study $FEV_1$ before and immediately after treatment on the study days remained similar to those recorded during the preliminary control test (table I). For every patient, distance run, duration of exercise, and heart-rate increase remained similar for each bout of exercise. There was no significant difference in postexercise changes in $FEV_1$ values—both absolute (table I) and percent (FIG. 1) between control and placebo, whereas the difference between placebo and furosemide was highly significant at all the time points. The mean (95% CI) maximum percent $FEV_1$ fall was 34.1 (38.3-29.8) in the control test, 33.8 (39.1-28.5) after placebo, and 11.5 (14.3-8.7) after furosemide.

Two-dose Study

Again, baseline values remained stable (table II), as did distance run, duration of exercise, and heart-rate increase. Post-exercise changes in $FEV_1$—absolute (table II) and percentage (FIG. 2)—for the control test were similar to those occurring after placebo. The effects of 14 to 28 mg furosemide differed significantly from those of placebo. The effects of 14 mg furosemide also differed from those of 28 mg furosemide. The mean (95% CI) maximum percent fall was 36.2 (44.2-28.7) in the control test, 34.6 (39.4-30.0) after placebo, 19.7 (28.2-11.3) after 14 mg furosemide, and 13.6 (21.2-6.0) after 28 mg furosemide.

Oral F Study

There was no significant differences between control, placebo and oral furosemide in the effects on absolute (table III) or percentage (FIG. 3) changes in $FEV_1$ after exercise, whereas inhaled furosemide showed a protective effect. The mean (95% CI) maximum percentage fall was 37.8 (46.2-29.4) in the control test, 35.3 (45.9-24.7) after placebo, 38.2 (47.1-29.3) after oral furosemide, and 15.2 (19.9-10.5) after inhaled furosemide.

In all the three studies furosemide was tolerated well; it did not induce changes in blood pressure or pulse rate.

Conclusion

This study has shown that inhaled furosemide prevents exercise-induced bronchoconstriction in asthmatic patients. The protection is dose-dependent and is not accompanied by any direct bronchodilator effect. Oral furosemide, in the dose given in our study (20 mg), was ineffective.

TABLE I

| | Effect of 28 mg Furosemide given as aerosol on post-exercise $FEV_1$ in 18 Asthmatic patients | | | | | | | | | |
|---|---|---|---|---|---|---|---|---|---|---|
| | Baseline | | Post-exercise changes at following times (min):* | | | | | | | |
| — | Pre-treat | Post-treat | 2 | 4 | 6 | 8 | 10 | 15 | 20 | 30 |
| Control | | | | | | | | | | |
| Mean | 3.67 (92.7) | 3.69 (93.3) | 0.78 | 1.08 | 1.10 | 1.09 | 1.05 | 0.90 | 0.79 | 0.50 |
| 95% CI | 4.05 (96.6) | 4.06 (97.1) | 0.96 | 1.30 | 1.31 | 1.27 | 1.25 | 1.08 | 1.02 | 0.63 |
| | 3.29 (88.8) | 3.33 (89.5) | 0.60 | 0.85 | 0.88 | 0.90 | 0.85 | 0.72 | 0.56 | 0.38 |
| Placebo | | | | | | | | | | |
| Mean | 3.70 (92.8) | 3.71 (93.7) | 0.74 | 1.01 | 1.07 | 1.07 | 1.02 | 0.90 | 0.84 | 0.53 |
| 95% CI | 4.08 (96.5) | 4.09 (97.6) | 0.93 | 1.24 | 1.30 | 1.28 | 1.24 | 1.12 | 1.04 | 0.71 |
| | 3.32 (89.1) | 3.34 (89.8) | 0.55 | 0.79 | 0.85 | 0.86 | 0.80 | 0.68 | 0.63 | 0.35 |
| t(vs control) | — | — | 0.65 | 1.01 | 0.49 | 0.27 | 1.50 | 0.00 | 0.60 | 0.49 |
| p | — | — | NS | NS | NS | NS | NS | NS | NS | NS |
| Furosemide | | | | | | | | | | |
| Mean | 3.65 (91.8) | 3.68 (91.7) | 0.18 | 0.34 | 0.35 | 0.31 | 0.30 | 0.23 | 0.16 | 0.09 |
| 95% CI | 4.05 (95.6) | 4.10 (95.4) | 0.31 | 0.48 | 0.50 | 0.44 | 0.43 | 0.33 | 0.26 | 0.16 |
| | 3.26 (87.9) | 3.26 (88.0) | 0.04 | 0.21 | 0.21 | 0.19 | 0.17 | 0.12 | 0.05 | 0.01 |
| t (vs placebo) | — | — | 6.60 | 9.47 | 10.60 | 11.00 | 8.80 | 8.27 | 7.03 | 5.67 |
| p | — | — | <0.001 | <0.001 | <0.001 | <0.001 | <0.001 | <0.001 | <0.001 | <0.001 |

$FEV_1$ expressed in liters; *Change from post-treatment values. Numbers in parentheses refer to % predicted. p calculated by paired Student's t test.

TABLE II

Effect of 14 mg or 28 mg Furosemide given as aerosol on post-exercise $FEV_1$ in 18 Asthmatic patients

| | Baseline | | Post-exercise changes at following times (min):* | | | | | | | |
|---|---|---|---|---|---|---|---|---|---|---|
| | Pre-treat | Post-treat | 2 | 4 | 6 | 8 | 10 | 15 | 20 | 30 |
| Control | | | | | | | | | | |
| Mean | 3.59 (90.1) | 3.70 (92.5) | 0.77 | 1.06 | 1.19 | 1.09 | 1.06 | 0.88 | 0.77 | 0.59 |
| 95% CI | 4.00 (95.7) | 4.15 (96.9) | 1.00 | 1.38 | 1.49 | 1.32 | 1.32 | 1.15 | 1.05 | 0.81 |
| | 3.18 (84.6) | 3.25 (88.1) | 0.53 | 0.74 | 0.89 | 0.86 | 0.80 | 0.60 | 0.49 | 0.38 |
| Placebo | | | | | | | | | | |
| Mean | 3.68 (94.1) | 3.71 (93.1) | 0.64 | 0.97 | 1.11 | 1.09 | 1.09 | 0.96 | 0.90 | 0.69 |
| 95% CI | 4.30 (100.7) | 4.16 (99.8) | 0.82 | 1.22 | 1.38 | 1.38 | 1.36 | 1.24 | 1.26 | 0.90 |
| | 3.06 (87.5) | 3.26 (86.3) | 0.46 | 0.72 | 0.84 | 0.81 | 0.81 | 0.67 | 0.54 | 0.47 |
| t (vs control) | — | — | 1.51 | 0.75 | 0.84 | 0.00 | 0.30 | 1.20 | 1.89 | 1.56 |
| p | — | — | NS | NS | NS | NS | NS | NS | NS | NS |
| Furosemide 14 mg | | | | | | | | | | |
| Mean | 3.69 (92.5) | 3.68 (92.0) | 0.38 | 0.63 | 0.55 | 0.53 | 0.50 | 0.46 | 0.38 | 0.32 |
| 95% CI | 4.18 (99.5) | 4.17 (98.3) | 0.62 | 0.94 | 0.85 | 0.76 | 0.76 | 0.68 | 0.57 | 0.50 |
| | 3.21 (85.4) | 3.19 (85.7) | 0.14 | 0.31 | 0.25 | 0.30 | 0.24 | 0.23 | 0.19 | 0.13 |
| t (vs placebo) | — | — | 3.23 | 4.03 | 7.13 | 6.05 | 5.50 | 4.00 | 3.70 | 3.66 |
| p | — | — | <0.025 | <0.01 | <0.001 | <0.001 | <0.001 | <0.005 | <0.01 | <0.025 |
| Furosemide 28 mg | | | | | | | | | | |
| Mean | 3.76 (94.9) | 3.80 (95.7) | 0.14 | 0.38 | 0.42 | 0.38 | 0.33 | 0.28 | 0.14 | 0.07 |
| 95% CI | 4.16 (100.6) | 4.18 (103.0) | 0.27 | 0.72 | 0.66 | 0.59 | 0.54 | 0.45 | 0.27 | 0.28 |
| | 3.36 (88.2) | 3.42 (88.3) | 0.00 | 0.03 | 0.17 | 0.16 | 0.11 | 0.10 | 0.02 | +0.14 |
| t (vs placebo) | — | — | 9.50 | 6.54 | 12.70 | 9.37 | 7.08 | 5.85 | 4.55 | 4.83 |
| p | — | — | <0.001 | <0.001 | <0.001 | <0.001 | <0.001 | <0.001 | <0.005 | <0.005 |
| t (vs 14 mg) | — | — | 3.63 | 8.82 | 3.28 | 5.12 | 3.86 | 3.92 | 3.45 | 2.87 |
| p | | | <0.01 | <0.001 | <0.01 | <0.005 | <0.01 | <0.01 | <0.01 | <0.025 |

$FEV_1$ expressed in liters; *Change form post-treatment values. Numbers in parentheses refer to % predicted.

TABLE III

Effect of 20 mg Oral Furosemide or 28 mg inhaled Furosemide post-exercise $FEV_1$ in 8 Asthmatic patients

| | Baseline | | Post-exercise changes at following times (min):* | | | | | | | |
|---|---|---|---|---|---|---|---|---|---|---|
| | Pre-treat | Post-treat | 2 | 4 | 6 | 8 | 10 | 15 | 20 | 30 |
| Control | | | | | | | | | | |
| Mean | 3.81 (90.6) | 3.80 (90.4) | 0.91 | 1.17 | 1.33 | 1.32 | 1.24 | 1.19 | 1.04 | 0.66 |
| 95% CI | 4.28 (95.5) | 4.23 (95.7) | 1.26 | 1.52 | 1.67 | 1.68 | 1.56 | 1.53 | 1.38 | 0.78 |
| | 3.34 (85.7) | 3.37 (86.0) | 0.55 | 0.82 | 0.98 | 0.95 | 0.92 | 0.86 | 0.71 | 0.55 |
| Placebo | | | | | | | | | | |
| Mean | 3.91 (92.1) | 3.83 (90.8) | 0.86 | 1.09 | 1.21 | 1.23 | 1.19 | 1.08 | 1.03 | 0.94 |
| 95% CI | 4.42 (98.6) | 4.38 (97.6) | 1.17 | 1.43 | 1.56 | 1.60 | 1.57 | 1.42 | 1.40 | 1.31 |
| | 3.40 (85.6) | 3.28 (84.0) | 0.55 | 0.75 | 0.87 | 0.85 | 0.82 | 0.73 | 0.67 | 0.56 |
| t(vs control) | — | — | 0.50 | 0.88 | 2.08 | 1.22 | 0.41 | 1.82 | 0.16 | 2.69 |
| p | — | — | NS | NS | NS | NS | NS | NS | NS | <0.05 |
| Oral furosemide | | | | | | | | | | |
| Mean | 3.73 (89.4) | 3.81 (90.7) | 0.84 | 1.17 | 1.25 | 1.21 | 1.21 | 1.13 | 1.00 | 0.88 |
| 95% CI | 4.22 (94.4) | 4.22 (95.7) | 1.11 | 1.42 | 1.54 | 1.53 | 1.52 | 1.47 | 1.33 | 1.26 |
| | 3.25 (84.4) | 3.39 (85.7) | 0.57 | 0.91 | 0.96 | 0.89 | 0.89 | 0.78 | 0.67 | 0.50 |
| t(vs placebo) | — | — | 1.25 | 1.47 | 0.68 | 0.18 | 0.22 | 1.45 | 0.56 | 0.76 |
| p | — | — | NS | NS | NS | NS | NS | NS | NS | NS |
| Inhaled furosemide | | | | | | | | | | |
| Mean | 3.73 (89.0) | 3.80 (93.4) | 0.36 | 0.49 | 0.57 | 0.43 | 0.40 | 0.40 | 0.28 | 0.18 |
| 95% CI | 4.19 (95.1) | 4.19 (95.8) | 0.58 | 0.69 | 0.98 | 0.66 | 0.63 | 0.64 | 0.50 | 0.35 |
| | 3.27 (84.1) | 3.40 (86.9) | 0.13 | 0.28 | 0.15 | 0.19 | 0.17 | 0.16 | 0.07 | 0.00 |
| t(vs placebo) | — | — | 3.58 | 8.12 | 7.80 | 7.20 | 6.30 | 5.80 | 4.77 | 5.03 |
| p | — | — | <0.01 | <0.001 | <0.001 | <0.001 | <0.001 | <0.001 | <0.005 | <0.005 |
| t (vs oral) | — | — | 4.04 | 11.41 | 5.35 | 11.37 | 9.02 | 6.44 | 5.35 | 5.32 |
| p | — | — | <0.005 | <0.001 | <0.005 | <0.001 | <0.001 | <0.001 | <0.005 | <0.005 |

$FEV_1$ expressed in liters; *Change from post treatment values. Numbers in parentheses refer to % predicted.

post-exercise percentage changes in FEV$_1$ from baseline in 8 asthmatic patients.

Vertical line represent 95% CI. Asterisks refer to differences between placebo and furosemide 14 mg, solid triangles refer to differences between the two doses of furosemide. $\Delta$ or * p<0.05; $\Delta\Delta$ or  p<0.01; * p<0.001.

Figure 1:
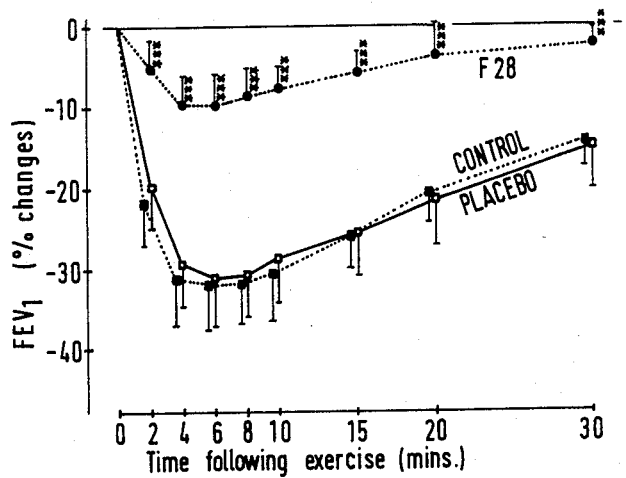
FIG. 1 shows the effect of approximately 28 mg furosemide given by inhalation on mean (95% CI) post-exercise percentage changes in $FEV_1$ from baseline in 18 asthmatic patients. Vertical lines represent 95% CI. *** $p<0.001$ (paired student's test) for difference between placebo and inhaled furosemide at individual points.
Figure 2:
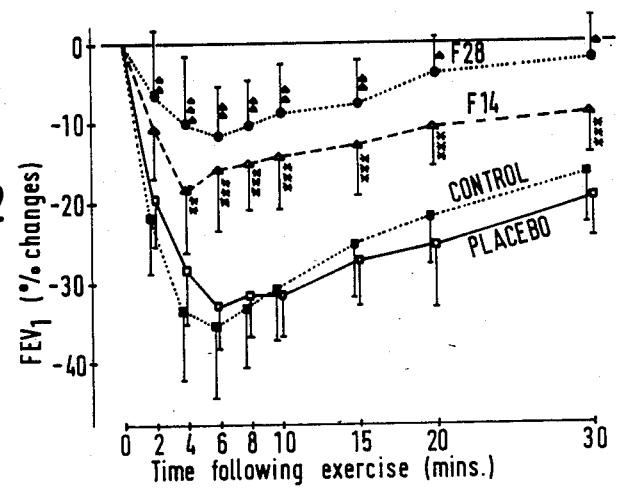
FIG. 2 shows the effect of approximately 28 mg or 14 mg furosemide given by inhalation on mean (95% CI)
Figure 3:
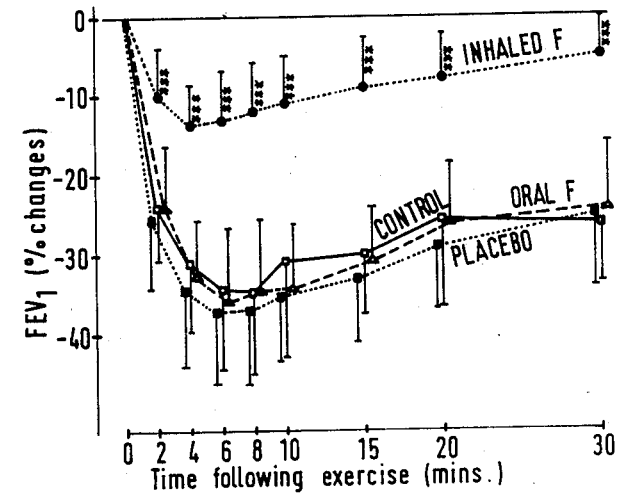

FIG. 3 shows the effect of approximately 28 mg furosemide given as aerosol or 20 mg given orally in post-exercise percentage changes in FEV$_1$ from baseline in 8 asthmatic patients.

*** p<0.001 (paired Student's test) for difference between placebo and inhaled furosemide.

2. Inhaled furosemide is also highly effective in preventing ultrasonically nebulized water (UNH$_2$O) bronchoconstriction:

SUBJECTS AND METHODS 16 adult (25-54 yr.) stable (mean, 95% FEV$_1$: 87.9±7.9% predicted) asthmatic (5 atopics) patients (6 men), responsive to UNH$_2$O, were tested on 2 occasions. On each occasion, they were challenged with UNH$_2$O generated by a Mistogen nebulizer (model EX 143) adjusted to deliver 2 ml/min (3 exposures of 30 s, 60 s, 120 s at 2 min intervals) immediately after receiving, in random order and double blind, either inhaled F (given as ®Lasix Hoechst, as a 10 mg ml solution containing NaCl 7.0 mg, NaOH to reach pH 9, and water to make up 1 ml) or placebo (the diluent solution of F). The amount of F delivered into the mouth by means of a jet nebulizer (Flatus, Mefar, Borezza (Br) Italy) was about 28 mg.

F did not change baseline sRaw (measured in a closed type body-plethysmograph) but prevented to large extent its increase after UNH$_2$O:

| | $\Delta$ | | |
|---|---|---|---|
| | 30 s | 60 s | 120 s |
| placebo | 7.4 | 19.7 | 33.3 |
| 95% C.I. | (3.0–15.4) | (9.4–30.0) | (9.0–47.5) |
| furosemide | 1.4 | 3.9 | 8.7 |
| 95% C.I. | (−0.3–3.1) | (−0.3–8.1) | (2.1–15.3) |

This corresponds to a %-protection of 80.5 (69.2–91.3). Oral furosemide (20 mg) was ineffective in 2 patients.

Conclusion

Furosemide is highly effective in preventing UNH$_2$ bronchoconstriction.

3. Inhaled furosemide prevents allergen induced bronchoconstriction in atopic asthmatics:

SUBJECTS AND METHODS 10 stable asthmatic patients (8 male) aged 17 to 48 yr with positive skin tests to dermatophagoides pteronyssinus (2 p), parietaria (2 p) and grass mixt (6 p) were studied out of the pollen season at the same time of the day, on 2 occasions with 4–7 days in between. On each occasion they were challenged with the same dose of antigen (Alpha fractions, Dome, Hollister-Stier) that had induced a FEV$_1$ fall of at least 20% in a preliminary dose-response study. Allergens were administered by means of a dosimeter (Mefar, Bovezza, (Br) (Italy)) immediately after pretreatment with either F (about 28 mg) or placebo (the diluent of F), given in random order and double blind by means of a jet nebulizer (Flatus, Mefar, Bovezza (Br) (Italy)).

sRaw (closed type plethysmograph) and FEV$_1$ (dry spirometer, Vitalograph) were measured immediately before and after pretreatment and then at 5, 10, 20, 30, 45, 50 min after allergen challenge. Baseline FEV$_1$ and sRaw values before and after pretreatment did not differ significantly on the 2 study days. F attenuated markedly the bronchial response to allergens:

| | mean max. % change (95% CI) from baseline | |
|---|---|---|
| | sRaw (+) | FEV$_1$ (−) |
| placebo | 256 | 28.5 |
| | (129.1–382.9) | (12.1–44.5) |
| furosemide | 31.5 | 8.4 |
| | (22.8–40.2) | (11.8–4.9) |

The mean (95% CI) combined protective effect using the area under sRaw and FEV$_1$ curves was 79.4 (72.4–86.4).

Conclusion

It is evident that F prevents allergen-induced immediate bronchoconstriction.

I claim:

1. A method of treatment of asthma characterized in that furosemide is inhaled.

2. The method according to claim 1 characterized in that a single dose of 0.1–50 mg furosemide is administered, calculated on an adult human of about 75 kg weight.

3. The method according to claim 1 characterized in that a single dose of 1–20 mg furosemide is administered, calculated on an adult human of a weight of about 75 kg.

* * * * *